United States Patent [19]

Thornton

[11] Patent Number: 4,718,904
[45] Date of Patent: Jan. 12, 1988

[54] INTRAOCULAR LENS FOR CAPSULAR BAG IMPLANTATION

[75] Inventor: Spencer P. Thornton, Nashville, Tenn.

[73] Assignee: Eye Technology, Inc., St. Paul, Minn.

[21] Appl. No.: 819,230

[22] Filed: Jan. 15, 1986

[51] Int. Cl.⁴ .............................................. A61F 2/16
[52] U.S. Cl. ......................................................... 623/6
[58] Field of Search ............................................ 623/6

[56] References Cited

U.S. PATENT DOCUMENTS

| | | |
|---|---|---|
| Re. 31,963 | 8/1985 | Kelman ................... 623/6 |
| Re. 31,998 | 10/1985 | Myers ..................... 623/6 |
| 4,092,743 | 6/1978 | Kelman ................... 623/6 |
| 4,110,848 | 9/1978 | Jensen .................... 623/6 |
| 4,190,049 | 2/1980 | Hager et al. ............. 623/6 |
| 4,242,762 | 1/1981 | Tennant .................. 623/6 |
| 4,244,060 | 1/1981 | Hoffer .................... 623/6 |
| 4,249,271 | 2/1981 | Poler ...................... 623/6 |
| 4,253,200 | 3/1981 | Kelman ................... 623/6 |
| 4,280,232 | 7/1981 | Hummel .................. 623/6 |
| 4,285,072 | 8/1981 | Morcher et al. ......... 623/6 |
| 4,328,595 | 5/1982 | Sheets .................... 623/6 |
| 4,340,979 | 8/1982 | Kelman ................... 623/6 |
| 4,343,050 | 8/1982 | Kelman ................... 623/6 |
| 4,354,360 | 12/1982 | Ong ........................ 623/6 |
| 4,361,913 | 12/1982 | Streck .................... 623/6 |
| 4,363,143 | 12/1982 | Callahan ................. 623/6 |
| 4,404,694 | 9/1983 | Kelman ................... 623/6 |
| 4,409,691 | 10/1983 | Levy ...................... 623/6 |
| 4,412,359 | 11/1983 | Myers ..................... 623/6 |
| 4,418,431 | 12/1983 | Feaster ................... 623/6 |
| 4,424,597 | 1/1984 | Schlegel ................. 623/6 |
| 4,449,257 | 5/1984 | Koeniger ................. 623/6 |
| 4,473,910 | 10/1984 | Grinder ................... 623/6 |
| 4,477,931 | 10/1984 | Kelman ................... 623/6 |
| 4,495,665 | 1/1985 | Kelman ................... 623/6 |
| 4,530,117 | 7/1985 | Kelman ................... 623/6 |
| 4,534,069 | 8/1985 | Kelman ................... 623/6 |
| 4,535,488 | 8/1985 | Haddad ................... 623/6 |
| 4,547,915 | 10/1985 | Castleman .............. 623/6 |
| 4,601,720 | 7/1986 | Sinskey ................... 623/6 |

FOREIGN PATENT DOCUMENTS

WO83/01568  5/1983  PCT Int'l Appl. ............ 623/6

OTHER PUBLICATIONS

The Lindstrom Centrex Style 20 Posterior Chamber Lens, advertisement brochure, Surgidev Corp., 1421 State St., Santa Barbara, CA 93101, 1981, 4 pages.
American Medical Optics Model PC-11 Posterior Chamber Intraocular Lenses (advertisement brochure), 4 pages, Aug. 1981.
Lens Styles from Cilco, advertisement brochure, Cilco (6 pages) pp. 1, 4, & 6 cited, Oct. 1982.
Intraocular Lens Implantation-Techniques & Complications, (book) by Clayman et al., The C. V. Mosby Company, 1983, pp. 150 & 151, Kratz/Sinskey Lens in FIGS. 5–12.
Interspace Lenses from Intermedics (advertisement page by Intermedics Intraocular) in Surgery News, Aug. 1, 1985, vol. 3, No. 15, Interspace U159B Modified C-Loop with Eyelet Lens.

Primary Examiner—Ronald L. Frinks
Attorney, Agent, or Firm—Cahill, Sutton & Thomas

[57] ABSTRACT

A convex anterior or convex posterior thin-edged intraocular lens is supported within the capsular bag adjacent the posterior capsule by a pair of curved haptics angled anteriorly to retain the intraocular lens posterior of and out of contact with the iris and pupil margin and to allow miosis. The compression and memory characteristics of the haptics gently stretch the posterior capsule against the intraocular lens to prevent both wrinkles and stress lines. Upon ciliary muscle contraction, the retention of the lens adjacent the posterior capsule also creates the potential for forward movement of the lens to permit the patient to change the focal power of the eye.

12 Claims, 5 Drawing Figures

INTRAOCULAR LENS FOR CAPSULAR BAG IMPLANTATION

The present invention relates to intraocular lenses and, more particularly, to intraocular lenses implanted within the capsular bag.

Numerous intraocular lenses have been created within the past fifteen years and many types of these lenses are presently being actively implanted in patients who have undergone intracapsular and extracapsular cataract extractions. Certain of these lenses are intended for attachment within the anterior chamber while others are intended for attachment within the posterior chamber. A few of the prior art lenses may be implanted within either the anterior or the posterior chamber. Of the lenses to be encapsulated in the posterior chamber, many configurations of the supporting loop or loops, sometimes referred to as haptics, have been developed, depending upon the nature of the attachment to be effected.

Some of the problems attendant intraocular lenses for implantation in the posterior chamber of the eye include decentration and glare from light striking the edge of the lens and/or a positioning holes within the pupillary zone. Posterior iris chafing may be caused by haptics located in the ciliar sulcus and rubbing by the lens against the back of the iris. Moreover, none of the prior art lenses readily permit accommodation by the patient; that is, the focal power is essentially invariable and established by the configuration of the lens as manufactured.

The intraocular lens of the present invention includes a pair of haptics which, in combination, define a reversed S shape for retaining the lens within the capsular bag. The haptics, being angled anteriorly from the lens to their outermost extremity, cause the lens to exert a slight pressure against the posterior capsule to prevent both wrinkles and stress lines. Moreover, with the continuing retention of the lens adjacent the posterior capsule, there is the potential for accommodation. The lens is formed with a very thin, smooth, rounded perimeter edge to permit implantation of a greater than six (6) millimeter diameter lens optic without incurring the necessity for increasing the chord length of an incision necessary for a conventional six (6) millimeter diameter lens and to provide an unobstructed optical area of six (6) millimeters or more in diameter.

It is therefore a primary object of the present invention to provide an intraocular lens for implantation in the capsular bag.

Another object of the present invention is to provide a posterior chamber intraocular lens which provides the potential for the patient to alter the focal power of the eye.

Yet another object of the present invention is to provide a posterior chamber intraocular lens which precludes iris rubbing and chafing.

Still another object of the present invention is to provide an intraocular lens which exerts a slight pressure upon a posterior capsule to eliminate wrinkles and stress lines.

A further object of the present invention is to provide an enlarged intraocular lens having both the perimeter and positioning holes outside the optic zone to eliminate light reflection therefrom.

A yet further object of the present invention is to provide an extremely thin, rounded and smooth peripheral lens edge which permits insertion through an incision having a chord length the same as that necessary for smaller diameter conventional intraocular lenses.

A still further object of the present invention is to provide an intraocular lens having very flexible haptics with plastic memory capability.

These and other objects of the present invention will become apparent to those skilled in the art as the description thereof proceeds.

The present invention will be described with greater specificity and clarity with reference to the following drawings, in which.

Figure 1:
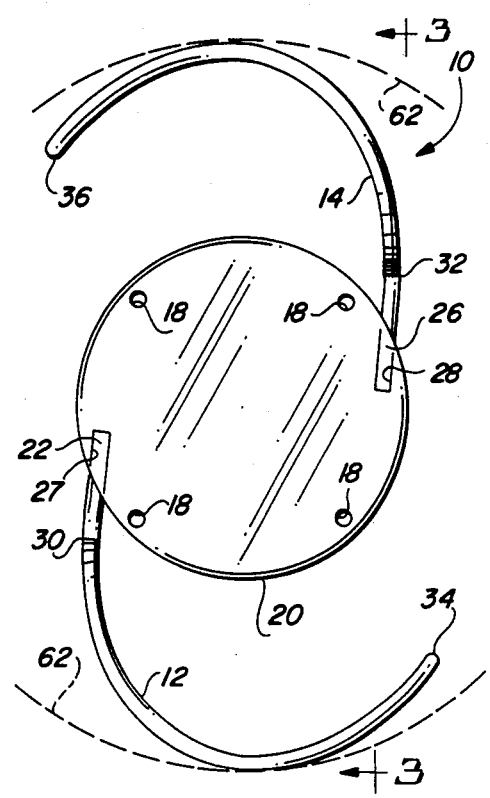
FIG. 1 is a frontal view of an intraocular lens constructed in accordance with the present invention.

Referring to FIG. 1, there is shown an intraocular lens 10 having haptics 12 and 14 extending in opposed directions from optic 16. The optic may include none or one or more positioning holes 18 dispersed adjacent peripheral edge 20. The function and purpose of these holes are that of aiding the surgeon in manipulating the intraocular lens during implantation. Preferably, optic 16 is sized to provide a clear optic zone interior of the positioning holes with a diameter of approximately six (6) millimeters.

Haptics 12 and 14 may be formed integral with optic 16. Alternatively, as illustrated, end 22 of haptic 12 may be inserted within an equivalent cross-section cavity 27 for retention therein. End 26 of haptic 14 may be similarly lodged within cavity 28. In one embodiment, the cross-sectional diameter of the optic and the haptics is thirteen (13) millimeters with a tolerance of 0.25 millimeters. Prolene or polypropylene is a plastic often used for haptics attached to an optic manufactured of polymethylmethacrylate (PMMA) as it is readily flexible to accommodate pressures exerted by and upon the eye as a result of muscular contraction, eye movement or pressures (and blows) imposed upon the eye. However, prolene or polypropylene does not have significant plastic memory. For purposes of the present invention, it is preferable that haptics 12 and 14 be manufactured of PMMA in order to take advantage of the plastic memory capability of such material. It is contemplated that optic 16 will also be manufactured from PMMA.

Figure 2:
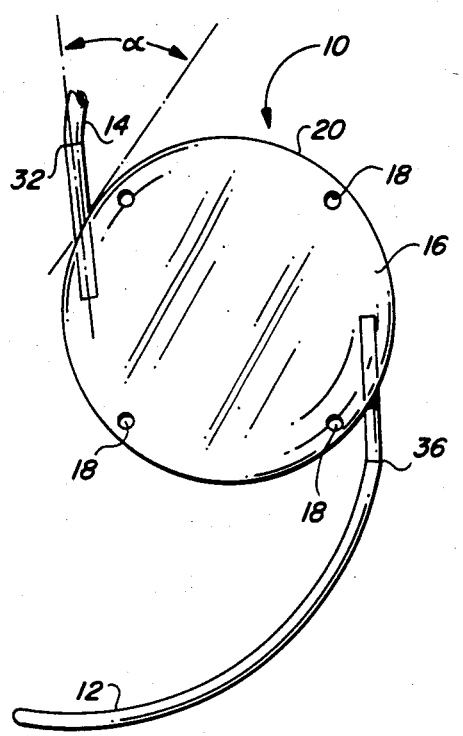
FIG. 2 is a partial posterior view of the intraocular lens illustrating certain features of the haptics.
Figure 3:
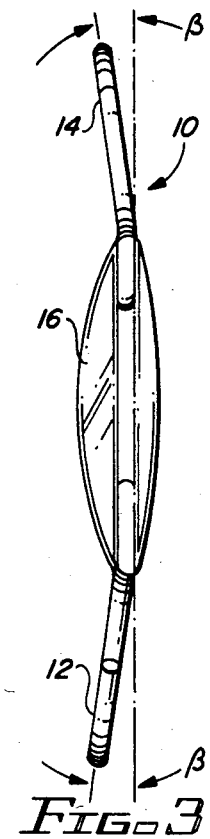
FIG. 3 is a side view of the intraocular lens.

Referring jointly to FIGS. 1, 2 and 3, further details of the haptic and optic construction and configuration will be discussed. Preferably, cavities 27 and 28 lie in the horizontal plane of the lens and at an angle of approximately 30° from a tangent at the point of attachment on edge 20 (or, from the plane of the sagital cross-section); this angle is represented by the letter alpha ($\alpha$) in FIG. 2. In the uncompressed or free standing state, each of haptics 12 and 14 present a curvature having a radius of approximately six (6) millimeters, as represented by haptic 12 in FIG. 2. As particularly shown in FIG. 3, each of haptics 12 and 14 is angled toward the anterior side of optic 16 at locations 30, 32, respectively, which locations are slightly beyond the point of protrusion of the haptics from the optic. Each haptic is angled at an angle of 7° from the horizontal plane of the lens, as represented by beta ($\beta$) in FIG. 3. Each of the haptics is fabricated from PMMA to provide the plastic memory capability of this material. To provide each haptic with sufficient flexibility and retain the superior stability and centration with material having plastic memory, each haptic has a diameter of approximately 0.14 millimeters with a tolerance of plus or minus 0.01 millimeters. Ends 34, 36 of haptics 12, 14, respectively, are rolled or rounded.

Most prior art intraocular lenses have an optic of six (6) millimeters in diameter. This size provides an acceptable compromise between the chord length of the incision necessary and the size of the optic area. By forming edge 20 of the optic to be extremely thin, rounded and smooth, an optic of 6.5 millimeters can be used without requiring any greater chord length incision than that for conventional six (6) millimeter diameter optics. A preferred radius for edge 20 is 0.12 millimeters with a tolerance of plus or minus 0.01 millimeters.

Optic 16 may be formed convex posterior/plano anterior, plano posterior/convex anterior or biconvex, depending upon the particular requirements of the patient and the judgment of the surgeon. For illustrative purposes, a biconvex optic is shown in FIG. 3 while a plano convex optic is illustrated in FIG. 5.

Figure 4:
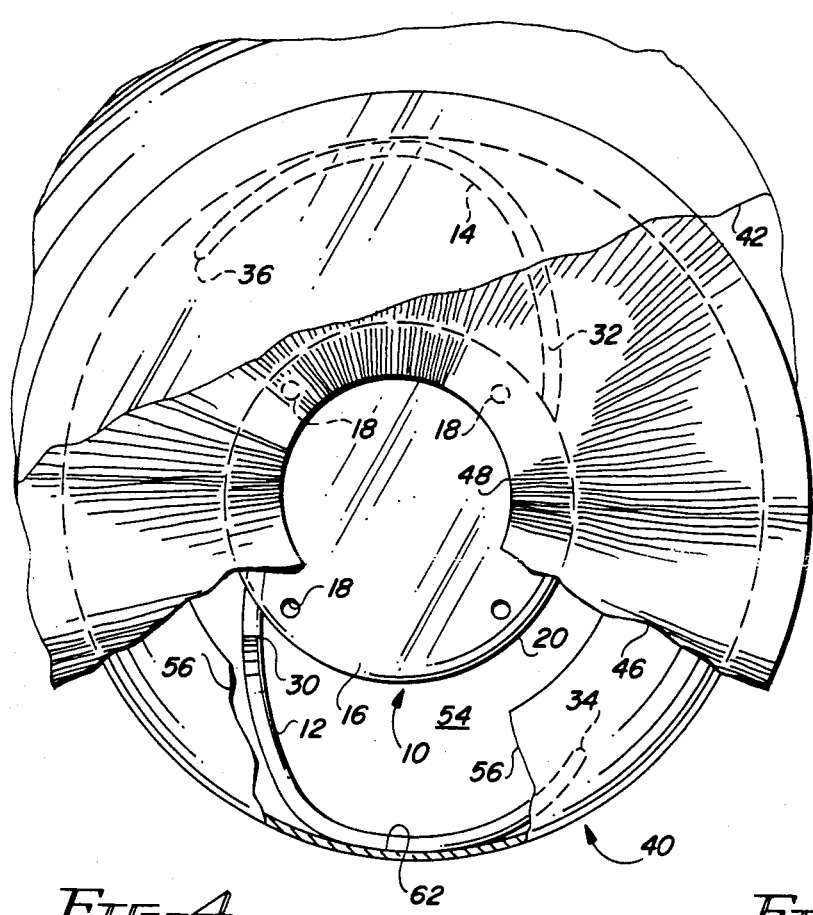
FIG. 4 is a frontal view illustrating an eye having the intraocular lens implanted.
Figure 5:
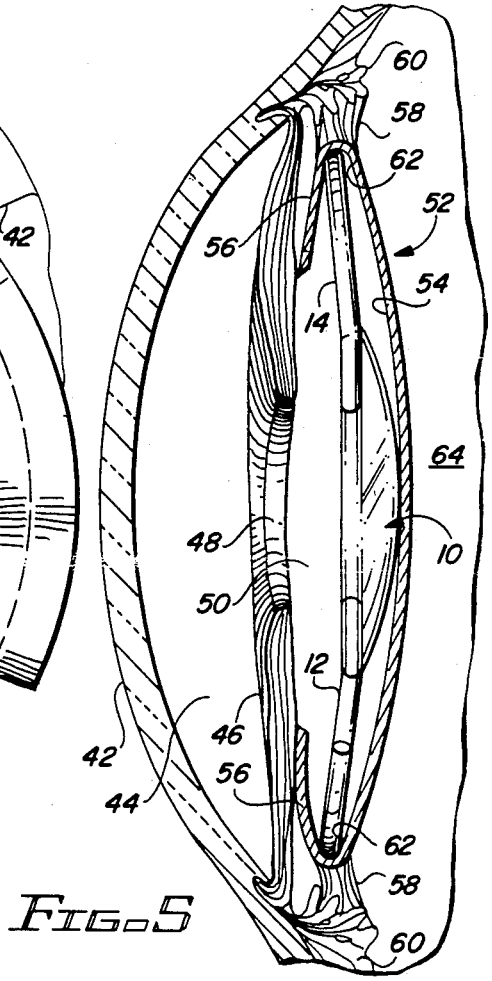
FIG. 5 is a partial cross-sectional view of an eye having the intraocular lens implanted.

Referring jointly to FIGS. 4 and 5, the operation of and function performed by intraocular lens 10 implanted within an eyeball 40 will be described. The eyeball consists of a cornea 42 that encapsulates anterior chamber 44 and iris 46. The iris defines pupillary aperature 48. Posterior chamber 50 includes capsular bag 52 adjacent vitreous cavity 64. Through extracapsular cataract surgery, the cataract or crystaline lens is removed to leave posterior capsule 54 and an annular anterior capsule flap 56. The remaining part of capsular bag 52 is retained by zonular fibers 58 attached to ciliary muscle 60.

Intraocular lens 10 may be implanted within capsular bag 52 by known surgical procedures. As pointed out above, the thin, smooth and rounded edge 20 of optic 16 permits the use of a chord length incision for conventionally configured six (6) millimeter diameter optics even though optic 16 is approximately 6.5 millimeters in diameter. Implantation of the intraocular lens, as illustrated in FIG. 5, permits the reversed S shape configuration of haptics 12 and 14 to distribute the forces exerted along a substantial length adjacent inner circumference 62 of capsular bag 52. The haptics, being manufactured of PMMA and to have a free standing curvature of approximately six (6) millimeters radius, will tend to return to such configuration due to the plastic memory capability of the PMMA. Upon implantation, haptics 12 and 14 will be somewhat compressed to a more acute curvature than their free standing curvature. Such recurving of the haptics tends to cause them to be in contact with diametrically opposed segments of the inner circumference 62 of capsular bag 52 for a substantial distance, as illustrated in FIGS. 1 and 4. The resulting stretching imposed upon the capsular bag will tend to assist in retention of the haptics within the capsular bag and prevent undesired haptic escape or withdrawal as a result of pressure or blow imparted to eyeball 40.

The seven degree (7°) angulation of the haptics posteriorly from the plane of the iris, as illustrated in FIG. 5, reduces iris and pupil margin contact of the haptics and optic to prevent posterior iris chafe and pupilary capture. Moreover, the haptics, being of PMMA and somewhat compressed within the capsular bag, also tend to induce a posteriorly oriented force upon optic 16. The combination of the seven degree (7°) posterior angulation in combination with the overall thirteen (13) millimeter diameter of intraocular lens 10 provides a very stable fixation and centration within the capsular bag. Additionally, the seven degree (7°) posterior angulation allows unimpeded pupillary miosis on accommodation and anterior movement on ciliary contraction with accommodative effort. Furthermore, the posterior bias placed upon optic 16 against posterior capsule 54 gently stretches the posterior capsule and the resulting contact creates a barrier to lens epithelial cell migration after implantation. The slight pressure exerted by optic 16 against the posterior capsule also tends to prevent wrinkles and stress lines in the posterior capsule. With the intimate contact between optic 16 and posterior capsule 54, there has been no pseudophakodenisis and experiments have also indicated a reduction in capsular opacification. Other benefits experienced have included: a reduction in the incidence of and the need for secondary posterior capsulotomies; no problems with elevated intraocular pressure; no problems with iris bleeding, iris chafe nor pupillary block; no tenderness to the patient; rare problems with CME or retinal detachment; and, a very high level of patient satisfaction.

As particularly illustrated in FIG. 4, the approximately 6.5 millimeter diameter of optic 16 permits positioning holes 18 to be radially outwardly of the six (6) millimeter optic zone. Such relocation increases by more than fifty percent (50%) the clear optical area when compared to presently available prior art lenses having a six (6) millimeter optic with positioning holes within such diameter. As is visually evident from FIG. 4, glare or reflection from the edges of positioning holes 18 and edge 20 of optic 16 is completely precluded by the overlap provided by iris 48 even with abnormally shaped or dilated pupils.

I claim:

1. An intraocular lens for implantation in the capsular bag of an eye upon which extracapsular cataract surgery has been performed, said intraocular lens comprising in combination:
   (a) an optic, said optic including a thin, rounded, polished perimeter edge having a radius of 0.12 millimeters with a tolerance of plus or minus 0.01 millimeters;
   (b) a pair of curved haptics extending in generally opposed directions from diametrically opposed locations of said optic for contactingly engaging the inner circumference of the capsular bag;
   (c) each haptic of said pair of haptics being angled anteriorly of said optic at an angle of seven degrees (7°) and at a location outwardly of the perimeter of said optic for locating said optic adjacent the posterior capsule of said capsular bag; and
   (d) each haptic of said pair of haptics being configured of a material having plastic memory for urging said optic against the posterior capsule upon implantation.

2. The intraocular lens as set forth in claim 1 wherein each haptic of said pair of haptics extends from said optic at an angle of approximately thirty degrees (30°) from the sagital plane of said optic.

3. The intraocular lens as set forth in claim 1 wherein each haptic, in an uncompressed state, of said pair of haptics defines a curve having a radius of six (6) millimeters.

4. The intraocular lens as set forth in claim 1 wherein said intraocular lens has an overall width of thirteen (13) millimeters.

5. The intraocular lens as set forth in claim 1 wherein said optic has a diameter of 6.5 millimeters.

6. The intraocular lens as set forth in claim 1 wherein said optic includes positioning holes formed within the perimeter of said optic.

7. The intraocular lens as set forth in claim 6 wherein said positioning holes are located outside of a six (6) millimeter diameter optic zone of said optic.

8. The intraocular lens as set forth in claim 1 wherein said optic includes a cavity for receiving each haptic of said pair of haptics.

9. The intraocular lens as set forth in claim 8 wherein each said cavity lies in a plane parallel with the horizontal plane of said optic and is aligned at an angle of thirty degrees (30°) with the sagital plane of said optic.

10. The intraocular lens as set forth in claim 1 wherein each said haptic is made of PMMA.

11. The intraocular lens as set forth in claim 1 wherein each said haptic has a diameter of 0.14 millimeters with a tolerance of plus or minus 0.01 millimeters.

12. The intraocular lens as set forth in claim 11 wherein each said haptic is made of PMMA.

* * * * *